United States Patent
Studer et al.

(10) Patent No.: US 10,024,866 B2
(45) Date of Patent: Jul. 17, 2018

(54) DEVICE FOR THE MICROSTRUCTURED GRAFTING OF PROTEINS ONTO A SUBSTRATE

(71) Applicants: ALVEOLE, Paris (FR); Centre National de la Recherche Scientifique—CNRS, Paris (FR); Université de Bordeaux Segalen, Bordeaux (FR)

(72) Inventors: Vincent Studer, Bordeaux (FR); Ammar Azioune, Merignac (FR)

(73) Assignees: ALVEOLE, Paris (FR); CENTRE NATIONAL DE LA RECHERCHE SCIENTIFIQUE—CNRS, Paris (FR); Universite de Bordeaux Segalen, Bordeaux (FR)

( * ) Notice: Subject to any disclaimer, the term of this patent is extended or adjusted under 35 U.S.C. 154(b) by 202 days.

(21) Appl. No.: 14/385,384

(22) PCT Filed: Mar. 14, 2013

(86) PCT No.: PCT/EP2013/055294
§ 371 (c)(1),
(2) Date: Dec. 23, 2014

(87) PCT Pub. No.: WO2013/135844
PCT Pub. Date: Sep. 19, 2013

(65) Prior Publication Data
US 2015/0147485 A1      May 28, 2015

(30) Foreign Application Priority Data

Mar. 14, 2012 (FR) .................................. 12 52304

(51) Int. Cl.
*G01N 33/00* (2006.01)
*G01N 33/68* (2006.01)
(Continued)

(52) U.S. Cl.
CPC ...... *G01N 33/6803* (2013.01); *B01J 19/0046* (2013.01); *B05C 9/12* (2013.01);
(Continued)

(58) Field of Classification Search
CPC .................................................. G01N 33/6803
(Continued)

(56) References Cited

U.S. PATENT DOCUMENTS

| 2002/0081582 A1* | 6/2002 | Gao ..................... B01J 19/0046 |
| | | 435/6.11 |
| 2003/0120035 A1* | 6/2003 | Gao ....................... C07H 19/06 |
| | | 530/333 |

(Continued)

FOREIGN PATENT DOCUMENTS

| EP | 1517178 A1 | 3/2005 |
| JP | 2006-133117 A | 5/2006 |

(Continued)

OTHER PUBLICATIONS

Fink, Jenny et al.; "Comparative study and improvement of current cell micro-patterning techniques"; Lab on a Chip, Royal Society of Chemistry, vol. 7, No. 6, Jun. 1, 2007; pp. 672-680 (9 pages).

(Continued)

*Primary Examiner* — Christine T Mui
*Assistant Examiner* — Emily R. Berkeley
(74) *Attorney, Agent, or Firm* — Osha Liang LLP

(57) ABSTRACT

A device for the microstructured grafting of proteins onto a substrate, comprising a substrate (7), a layer comprising a polyethylene glycol and being placed on the substrate, a matrix (10) of micromirrors for propagating the light in a first pattern and for replacing the first pattern with a second pattern. The microfluidic circuit is filled so as to bring a first aqueous solution containing a first protein into contact with the layer, a first microstructured image of the first pattern (Continued)

being formed on the layer to photoprint the first protein on the layer, and the microfluidic circuit is adapted to replace the first aqueous solution with a second aqueous solution containing a second protein so as to bring the second aqueous solution and the layer into contact, the first pattern being replaced with the second pattern in order to photoprint the second protein on the layer.

17 Claims, 1 Drawing Sheet

(51) Int. Cl.
*B01J 19/00* (2006.01)
*C40B 50/18* (2006.01)
*C40B 60/14* (2006.01)
*G01N 33/543* (2006.01)
*B82Y 30/00* (2011.01)
*B05C 9/12* (2006.01)
*B05D 1/00* (2006.01)
*B05D 3/06* (2006.01)

(52) U.S. Cl.
CPC ............... *B05D 1/00* (2013.01); *B05D 3/065* (2013.01); *B82Y 30/00* (2013.01); *C40B 50/18* (2013.01); *C40B 60/14* (2013.01); *G01N 33/54353* (2013.01); *B01J 2219/0059* (2013.01); *B01J 2219/0061* (2013.01); *B01J 2219/0074* (2013.01); *B01J 2219/00286* (2013.01); *B01J 2219/00337* (2013.01); *B01J 2219/00353* (2013.01); *B01J 2219/00389* (2013.01); *B01J 2219/00434* (2013.01); *B01J 2219/00439* (2013.01); *B01J 2219/00585* (2013.01); *B01J 2219/00605* (2013.01); *B01J 2219/00612* (2013.01); *B01J 2219/00626* (2013.01); *B01J 2219/00637* (2013.01); *B01J 2219/00659* (2013.01); *B01J 2219/00711* (2013.01); *B01J 2219/00725* (2013.01); *Y02P 20/582* (2015.11)

(58) Field of Classification Search
USPC .......................................................... 422/502
See application file for complete search history.

(56) References Cited

U.S. PATENT DOCUMENTS

2008/0206752 A1* 8/2008 Balakirev ........ G01N 33/54353
435/6.11
2008/0305964 A1* 12/2008 Bar-Ziv ................. B82Y 30/00
506/13

FOREIGN PATENT DOCUMENTS

| WO | 9941007 A2 | 8/1999 |
| WO | 9942813 A1 | 8/1999 |
| WO | 02072791 A2 | 9/2002 |
| WO | 2006084482 A1 | 8/2006 |

OTHER PUBLICATIONS

International Search Report dated Aug. 6, 2013 in corresponding International application No. PCT/EP2013/055294 (4 pages).
Written Opinion dated Aug. 6, 2013 in corresponding International application No. PCT/EP2013/055294 (5 pages).
Notice of Grounds for Rejection (Office Action) dated Feb. 7, 2017, issued by the Japan Patent Office in corresponding Japanese Patent Application No. JP 2014-561457, with English translation (6 pages).

* cited by examiner

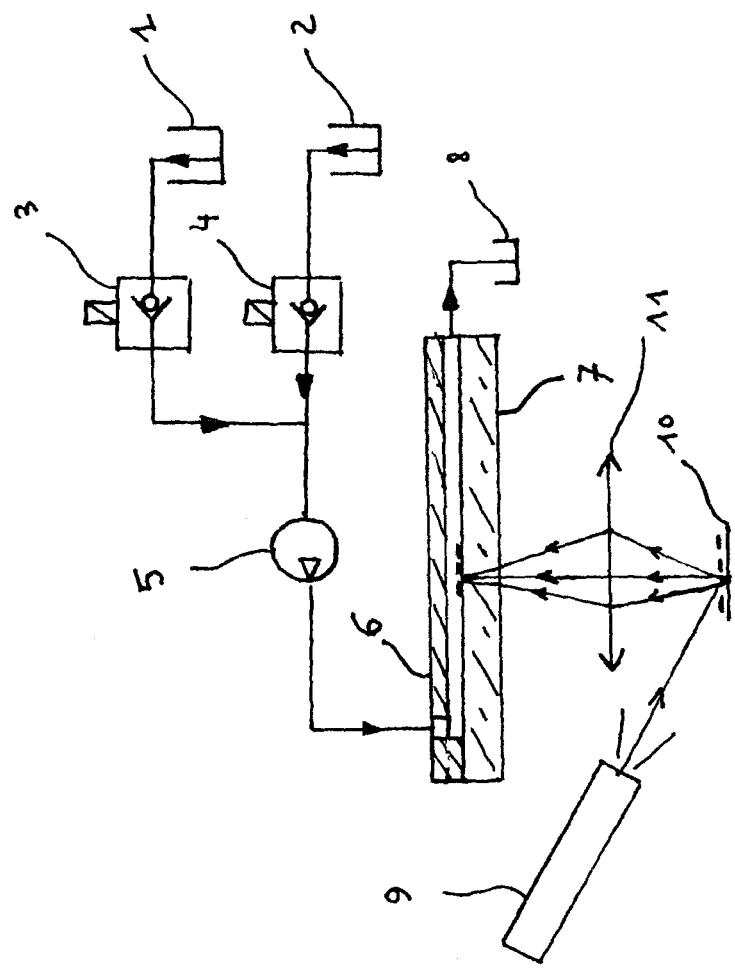

DEVICE FOR THE MICROSTRUCTURED GRAFTING OF PROTEINS ONTO A SUBSTRATE

TECHNICAL FIELD OF THE INVENTION

The invention relates to the general field of grafting of proteins onto a substrate according to patterns and to different concentrations, or protein printing or printing, the printing being obtained via a photochemical grafting means. The invention relates in particular to the field of photochemical grafting of a plurality of, i.e. of at least two, proteins onto a substrate, in an automated or automatable manner.

According to the present application, a protein is a biological macromolecule composed of a large number of chains of amino acids linked together by peptide bonds. A protein groups together a large number of amino acids, as opposed to peptides or oligopeptides, which contain a small number thereof. Proteins perform the functions of living cells.

The placing, on a substrate, of printed or surface layers of proteins in variable concentrations and different configurations or patterns is essential in the "in vitro" study, outside a living organism, of living cells since it makes it possible to recreate a protein environment which is as complex as desired, making "in vivo" tests, in particular on animals, increasingly unnecessary.

It is thus desirable in the prior art to have protein-printing means which are versatile or able to recreate, on a substrate, any pattern or design, using solutions of proteins or DNA or biological molecules, having given concentrations, for example contained in containers.

It is also desirable to be able to industrially print a plurality of proteins just as simply as a single protein.

SUMMARY OF THE PRIOR ART

The solutions envisioned in the prior art for the photochemical printing of one or more proteins on the same substrate suffer from considerable limitations which prevent the industrial application thereof.

Photochemical printing consists in chemically grafting or attaching molecules onto a surface, selectively in illuminated areas of the surface, by photoinduced adhesion.

A photochemical means for printing or grafting thus consists, in the prior art, generally, of a substrate, of an optical means for illuminating the substrate, of a fluidic means for bringing to the surface of the substrate a fluid containing a biological molecule in aqueous solution, such as a protein, an oligopeptide or DNA to be grafted onto the substrate, and of a molecule which is adhesive in the presence of the illumination or photoadhesive molecular glue, it being possible for said molecule either to be deposited onto the substrate or to be present in solution in the fluid with the protein.

When the adhesive molecule is in a solid layer deposited on the substrate, the photochemical grafting means is described as "layer grafting" in the present application.

When the adhesive molecule is in solution in a liquid in contact with the substrate, the photochemical grafting means is described as "solution grafting" in the present application.

With regard to layer grafting, which is a first grafting technique of the prior art, it uses a substrate treated with a solid layer which is integral with the substrate, which is photoadhesive for "small" molecules, which is to be printed, and which entirely covers the surface of the substrate between this substrate and a solution of small molecules. Said small molecules may be nucleotides in order to obtain DNA synthesis or peptides in order to obtain oligopeptide synthesis. Layer grafting is limited to molecules which are "small" compared with the size of a protein, in the sense that these molecules must not have a property of "non-specific" grafting onto the substrate, on the time scale of the use desired for the pattern printed on the substrate. The "non-specific" grafting property is observed when the size of a photoprinted molecule increases and this property may be characterized by an invasion of the substrate by the molecule outside the photoprinted patterns, in a time period which makes the substrate unusable in practice, due to screening of the printed pattern.

A common illuminating means for layer grafting consists, in a known manner, of a digitally controlled matrix of micromirrors which is capable of producing any pattern by tipping of each of the micromirrors of which it is composed, the matrix serving as an object at an objective which forms a microstructured image of any pattern, on the surface of the photoadhesive layer in contact with the solution containing the small molecules.

The printing of multiple small molecules is possible with a layer grafting means, although it requires protective layers for the molecules already deposited, before each new printing, thereby industrially complicating the use of this first technique.

However, since proteins have precisely the property of non-specific grafting, layer grafting means prove to be unsuitable, in the prior art, for the printing of a single protein and, a fortiori, for the printing of a plurality of proteins.

With regard to solution grafting, which is a second grafting technique of the prior art, it uses a substrate treated with a layer which is non-stick for a protein or antifouling and a glue which is photoadhesive both for the photoadhesive layer and for the protein, the photoadhesive glue being present in an aqueous solution containing the protein, said solution being brought into contact with the substrate and illuminated. The presence of a means dedicated to preventing non-specific grafting onto the substrate, in the form of the layer which is non-stick for proteins or antifouling, makes this second technique suitable for printing a single protein.

However, solution grafting uses a photolithography mask without any focusing optic and thus requires a film of solution of the protein and of the photoadhesive glue which is as thin as possible between the mask and the non-stick layer or antifouling, typically a few microns. A drop of solution squashed between a mask and a flat substrate, positioned in a fixed manner with respect to one another, is thus used. This optomechanical structure makes it a problem to generalize this second technique to the printing of a plurality of proteins for at least two reasons.

Firstly, it is difficult to envision automating the change of protein in the film by microfluidic pumping means, changing the solution. This is because the pressure drop increases as the thickness of the fluid film or film-coating decreases and this thickness must be minimal in order to maximize the optical quality; a typical thickness is 5 microns with an accuracy of 1 micron with regard to this value being considered desirable. Since relative variations in flatness of the substrate and of the mask are inevitable, it is found that the sizing of a microfluidic device suitable for an automatic change of solution, and therefore of protein, is difficult to envision for this second technique.

Secondly, it is imperative to use as many masks as there are proteins to be printed. This assumes a means of aligning or positioning the masks on the substrate, not only in the plane of this substrate but also with respect to the parallelism between the substrate and the mask, which optically influences the printed pattern. This means that each mask must be positioned three-dimensionally with respect to the substrate. Furthermore, in order to take into account the relative variations in flatness of the mask and of the substrate, it is, a priori, necessary to use masks and a substrate in which the flatness defects are very small or to recalculate each mask for each substrate, which is impossible to envision industrially.

Consequently, for these two reasons, the second technique cannot be easily used in the prior art for the industrial printing of more than one protein on a substrate.

The printing of several proteins, in sequence or one after the other, on a substrate in an automatable and industrial manner is therefore a difficult problem for the prior art and the designing of a rapid system for printing several proteins, on the same substrate, with a quality that is compatible with the reproduction of microstructured patterns or patterns with details having a fineness of about one micrometer or micron, does not appear to be envisionable in the art prior to the invention.

SUMMARY OF THE INVENTION

In this context, the invention is a device for the microstructured grafting of several proteins onto a substrate, which comprises a substrate, a layer, a matrix, a light source, an optical system, a first container for receiving a first aqueous solution, a second container for receiving a second aqueous solution and a microfluidic circuit, wherein the layer is placed on the substrate, the source is suitable for illuminating the matrix with the light, the matrix is suitable for propagating the light in a first structured pattern, the matrix comprises optical means for replacing the first structured pattern with a second structured pattern, the optical system is suitable for forming, on the layer, a first microstructured image of the first pattern, the circuit is suitable for containing the first aqueous solution, the circuit comprises an opening for bringing the first solution into contact with the layer at the opening, the circuit comprises microfluidic means for replacing the first solution with the second solution, and the layer comprises a polyethylene glycol at its surface.

In variants of the above device:
said matrix is a matrix of micromirrors propagating said light by reflection,
said optical system is a microscope objective,
said source is a laser emitting at an ultraviolet wavelength,
said ultraviolet wavelength is 365 nm.

The invention also relates to a method for the microstructured grafting of proteins onto a substrate using the above device and comprising the following steps:
filling the first container with a first aqueous solution comprising a benzophenone and a first protein,
filling said microfluidic circuit with said first aqueous solution so as to bring the first solution and said layer into contact, at said opening,
forming, by means of said light, said first microstructured image of said first structured pattern, on the layer, in order to photoprint said first protein on the layer.

In one variant of the above method:
said first protein is fluorescent.

The invention also relates to the above method comprising the following steps:

filling the second container with a second aqueous solution comprising the benzophenone and a second protein,
replacing said first aqueous solution with said second aqueous solution so as to bring the second solution and said layer into contact, at said opening,
replacing said first structured pattern with said second structured pattern in order to photoprint said second protein on the layer.

In one variant of the above method:
said second protein is fluorescent.

LIST OF THE FIGURES

The invention is described with reference to FIG. 1 for the numbers between parentheses.

FIG. 1 represents a first embodiment of the invention in the case of a system capable of printing two different proteins on the same substrate by means of patterns defined by a matrix of micromirrors. A laser (9) emitting in the ultraviolet range is, for this purpose, arranged so as to illuminate a matrix (10) of micromirrors. An objective (11) serving as an optical system, images the matrix (10), on a transparent substrate (7) via the interior of this substrate, on a first surface of the substrate. On the exterior of the substrate, in contact with this first surface, is a microchannel (6) which is part of a fluidic circuit comprising, in series with a first inlet of the microchannel, a micropump (5), a first container (1) which can feed the micropump when a first electrically controlled microvalve (3) is opened by a computer (not represented), and a second container (2) which can feed the micropump when a second electrically controlled microvalve (4) is opened by the computer; the microchannel of the circuit also comprises an outlet which opens into a run-off or drainage container (8).

DETAILED DESCRIPTION OF AT LEAST ONE EMBODIMENT OF THE INVENTION

In a first embodiment of the invention, a first protein is contained in a first container (1) and a second protein is contained in a second container (2).

The first protein is green fibrinogen, known under the name Fibrinogen-Alexa Fluor 488, and the second protein is red fibrinogen, known under the name Fibrinogen Alexa Fluor 546. It is also possible to choose fibronectin for one of the two proteins or for both, as a replacement for said fibrinogens. The following proteins: fibrinogen, fibronectin, laminin, collagen and vitronectin can also be used with the invention. Fluorescent proteins, such as, in particular, green fibrinogen and red fibrinogen, are advantageous for the invention, for the purposes of visualizing the printing produced on the substrate.

The first protein is diluted in a first fluid or first solution which is aqueous or buffered, contained in the first container, the first solution also comprising water and a first grafting means which is a benzophenone or benzoylbenzyltrimethylammonium chloride, in a water-soluble version of this product.

The second protein is diluted in a second fluid or a second solution which is aqueous or buffered, contained in the second container, the second solution also comprising water and a second grafting means which is also said benzophenone.

In any embodiment of the invention, a solution using a liquid other than water but which does not denature proteins may be used.

The first container is connected to a first microvalve (3) and the second container is connected to a second microvalve (4). The first microvalve and the second microvalve are connected to a micropump (5). The micropump is connected to a first end of a microchannel (6) surmounting a glass substrate (7), which is treated, on a first surface of this substrate, with a thin layer, of about 2 nm, consisting of polyethylene glycol or PEG. The substrate forms a cover for the microchannel which has an opening at the substrate, in such a way that a fluid, passing through the microchannel, is in contact with the first surface of the substrate or more specifically with the thin layer of PEG or else with the treated substrate.

The microchannel is open at a second end and allows a liquid passing through it to escape into a run-off container (8). Where appropriate, if no pollution of the containers is to be feared, a system for recycling the fluid escaping from the microchannel, into the container from which the fluid comes, might be provided.

A micropump suitable for the invention will, for example, be a non-reversible constant-delivery micropump.

A microvalve suitable for the invention may be in particular a non-return valve normally blocked by the fluid and which is opened by electrical control. Any other hydraulic slide valve which enables the switching or the multiplexing of the containers in a single duct connected to the micropump will be suitable for the invention.

Throughout the present application, the prefix "micro" for terms in the technical field of fluidics is not limiting, in terms of dimension, to objects of the size of a micron, but signifies that the fluidic elements used to form the fluidic circuit or system of the invention are sized in as small as possible a way in order to avoid wasting the first solution and the second solution when they are brought into contact with the substrate by the fluidic elements of said circuit and then discharged into the run-off container. If a printing surface or printing surface of the substrate is fixed, for example at a 1 cm-by-1 cm square, a depth of the microchannel or extension of the microchannel from the first surface, outside this first surface, may thus be 200 microns, so as to obtain a volume of 20 microliters of solution above the printing surface. It will thus be possible to limit the renewal to small amounts of solution and of protein, by virtue of the microfluidic aspect of certain means of the invention, thereby constituting an industrial advantage.

Throughout the present application, the words "printing on the substrate" are considered to be synonymous with "printing on the layer" when the layer is a surface treatment of the substrate of low thickness compared with that of the substrate. This is the case with the layer and the substrate in the invention.

In the present application, the substrate is glass or ITO or any other material which is transparent if light must pass through it in order to obtain the printing. Likewise, the layer is transparent if light must pass through it in order to obtain the printing. In the case where a substrate would be naturally non-stick for proteins or antifouling, the layer would then be understood to be a surface layer of the substrate on which the grafting takes place, without departing from the teaching of the invention.

The sizing of a fluidic or microfluidic circuit, given the above indications, which is suitable for the invention can be carried out by those skilled in the art of microfluidics, without particular difficulty, with their usual knowledge. The invention will thus comprise a microfluidic circuit placed between the layer and the first and second container of aqueous solution containing the first and second protein, respectively. In a generalization of the invention in terms of its fluidic circuit, the microfluidic circuit will comprise means for bringing an outlet of the circuit into contact with a plurality of aqueous solutions each containing a particular protein and benzophenone, as, for example, a function of an automatic control by a computer according to a programmed choice. In the embodiment presented, wherein the fluidic architecture corresponds to a multiplexer with two inlets, one per container, and an outlet, at the microchannel, it is possible to add containers and inlets to the multiplexer via known fluidic means in order to increase the number of protein solutions that can fill the microchannel. The invention is thus presented in this first embodiment as an illustration of its structure with two proteins, without being particularly limited to this number.

Furthermore, in this first embodiment of the invention, an ultraviolet light source (9), which is an ultraviolet laser emitting at a wavelength of 365 nm, optionally pulsed in order to benefit from a high optical power, is included in the device and illuminates a planar matrix (10) of micromirrors which is digitally controlled by a computer (not represented). This matrix makes it possible to produce an object, each pixel of which can be individually controlled so as to form an object pattern, of any complexity, having a number of independent points equal to the number of micromirrors of the matrix. Each micromirror can be reduced to one dark or illuminated pixel, the matrix forming a pattern in its plane, i.e. a two-dimensional pattern. This matrix is imaged by an objective (11) optimized for ultraviolet light and forming an image of the matrix on the first surface of the substrate, in the middle of the substrate. The optical system or objective may be an inverted microscope, i.e. a microscope objective in which the direction of the light is inverted, so as to convert the matrix structured in a pattern having a resolution of about 10 microns into a microstructured image with a resolution or fineness of about 1 micron, via a magnification of less than 1, of about $\frac{1}{10}$.

The substrate is advantageously arranged in such a way that the light emitted by the laser first passes through this substrate before the image forms on its first surface. In other words, if the substrate has a first thickness extending between the second surface and the first surface, the second surface is touched by the ultraviolet light and then the first surface is touched by the ultraviolet light, in the direction of propagation of the light. This arrangement is referred to in the application by the expression "the substrate is illuminated from the interior", as opposed to the situation where the light encounters the first and the second surface in this order, which is referred to by the expression "the substrate is illuminated from the exterior". The illumination via the interior of the substrate makes it possible to be freed from the optical defects of the solution; this is a preferred implementation variant for the invention.

The substrate, light, benzophenone, PEG and protein elements are chosen as follows: for a given protein, the PEG is chosen as layer which is non-stick for the protein or antifouling but adhesive on the substrate, the benzophenone is chosen as glue which is adhesive for the protein and the layer, under illumination by the light. It is thus possible to determine other materials which make it possible to implement the invention for other proteins.

A device for photoprinting, in a first structured pattern, the first protein on the treated substrate is then obtained by means of a method comprising the following steps:

filling the microfluidic circuit with the first aqueous solution containing the first protein until the first solution and the layer of PEG are brought into contact, at the microchannel opening covered by the layer of PEG deposited on the substrate, forming, by means of said light, a first microstructured image, reduced by the microscope objective, of a first structured pattern, on the layer, in order to photoprint the first protein on the layer.

The invention thus takes up a first configuration, in relation to printing by means of the first container. A complex pattern for printing two proteins on the substrate can be easily produced on the basis of this first configuration, by replacing the first solution with the second solution and by replacing, with a second pattern, the first pattern displayed or reflected or propagated or transmitted by the matrix.

Thus, in order to obtain the first configuration, it is sufficient to open the first microvalve and close the second microvalve and to pump with the micropump so as to obtain the first protein at the layer. In order to obtain the first microstructured pattern on the layer, it is also sufficient to supply power to the light source and to select a first pattern on the matrix.

It should be considered that, in this first embodiment, the matrix of micromirrors has optical means for replacing the first structured pattern with a different second structured pattern.

It should also be considered that, in this first embodiment, the microfluidic circuit, defined as means for feeding with solution the area formed by the layer which is non-stick for proteins or antifouling, has microfluidic means for replacing the first solution with a second solution, at the layer.

It is then simple to replace the first aqueous solution with the second aqueous solution at the layer and to replace the first structured pattern with a second structured pattern on the matrix, the second microstructured image of said second pattern then forming on the layer.

Thus it results a second configuration of the invention in this first embodiment, wherein the second protein is photoprinted on the layer according to the image of the second pattern.

It is also possible to replace the first solution with a plurality of aqueous solutions of proteins and of molecules which are photoactivatable (sulfo-SANPAH or sulfosuccinimidyl 6-((4-azido-2-nitrophenyl)amino)hexanoate, anthraquinone-2-sulfonic acid sodium salt monohydrate, benzophenone-4-maleimide, benzophenone-4-isocyanate, 4-azido-2,3,5,6-tetrafluorobenzoic acid, succinimidyl ester) and to replace the first structured pattern of the matrix of micromirrors with a plurality of patterns, which is associated with a desired printing for a protein of a solution of the plurality, so as to obtain a microstructured image thereof on the layer of PEG. The invention is thus suitable for easy printing of a plurality of proteins on a substrate in arbitrarily chosen patterns, therefore arbitrarily complex printing.

It is also possible to add a third rinsing line by adding a third container filled with a buffer solution, by connecting it to a third automatically controlled microvalve, of the same type as the first and second microvalve, and by connecting the outlet of this third valve to the micropump. The rinsing buffer solution may in particular be distilled water or physiological saline or other protein-washing solutions (ionic or nonionic surfactants: Tween 20, Triton X100).

Thus the invention has a particular interest for use in the rapid and versatile printing of several proteins on a substrate, using several containers and with a high and long-lasting chemical contrast, i.e. without non-specific grafting. The chemical contrast is conveniently defined, for the present application, as the difference in concentration of the same protein in distinct places, said difference being divided by the sum of the concentrations of said same protein, in these same places.

The invention also has a capacity to function industrially since it should also be noted that, in all the configurations of the invention, a computer can advantageously control each of the elements of the invention: light source, matrix of micromirrors, fluidic circuit (micropump, microvalves), by providing them with automatic controls known from the prior art.

The use for printing two proteins of the invention is, for example, obtained according to two configurations.

In a first configuration for use, the first container (1) is connected, via the open first microvalve (3), to the micropump (5) and to the microchannel (6), and the second microvalve (4) is closed so as to prevent mixing, in the microfluidic circuit, of the fluids contained in the first and second containers. A first fluid containing a first protein thus flows from the first container to the microchannel and then escapes into the run-off container (8).

In this first configuration, a first pattern is drawn on the matrix (10) of micromirrors by a computer (not represented) and the image of this first pattern or first optical pattern is formed on the first surface of the substrate. The first container contains a first fluid containing a first protein and a first means for solution-grafting of the first protein onto the first surface, under ultraviolet illumination. The image of the first optical pattern is translated in the form of a first chemical pattern of the first protein by the first grafting means, having the same spatial extent as the first optical pattern and which is superimposable thereon.

In a second configuration for use, the second container (2) is connected, via the open second microvalve (4), to the micropump (5) and to the microchannel (6), and the first microvalve (3) is closed so as to prevent mixing of the fluids contained in the first and second containers. A second fluid containing a second protein thus flows from the second container to the microchannel and then escapes into the run-off container (8). In this second configuration, a second pattern is drawn on the matrix (10) of micromirrors by the computer and the image of this second pattern or second optical pattern is formed on the first surface of the substrate. The second container contains a second fluid containing a second protein and a second means for solution-grafting of the second protein onto the first surface, under ultraviolet illumination. The image of the second optical pattern is translated in the form of a second chemical pattern of the second protein by the second grafting means, having the same spatial extent as the second optical pattern and which is perfectly superimposable thereon, the substrate not having moved throughout the use, which constitutes a considerable advantage for printing a plurality of proteins, for which the operations performed for the second protein can be repeated for each protein remaining to be printed, without difficulty.

The invention can also be used to produce a gradient of concentration of the same protein, in particular by modulating the illumination time of the surface treatment of the substrate or by using the same time but by selecting containers containing the same protein at different concentrations.

Gradients of green fibrinogen (Alexa 488), of red fibrinogen (Alexa 546) and of yellow fibrinogen (Alexa 532) have in particular been obtained with the invention by projecting the image of a grid with different illumination times.

Regarding the invention in general and for other embodiments or uses, the following considerations apply:

any matrix other than micromirrors which propagates light in an optically contrasted pattern is suitable for the invention. A liquid crystal spatial modulator operating by transmission rather than by reflection or by absorption of light would be suitable for the invention;

any means of creating a pattern and of producing the image thereof on the layer is suitable for the invention. A source-light transmission system, creating a contrasted pattern or luminous pattern or pattern, by light transmission, the pattern being reproduced by the objective and imaged onto the first surface of the substrate by the objective, would also be suitable for the invention. The operation by reflection of the matrix of micromirrors, combined with an inverted microscope objective, of the first embodiment of the invention is therefore an example of an illumination means or of a spatial modulator of the source light, for the purpose of the invention.

In all its embodiments, the invention has practical advantages for the printing of several proteins:

Optical and dimensional stability of the system, no dismantling being necessary, while making it possible to limit the non-specific grafting of proteins, essential in the application, through the use of PEG as printing layer and of benzophenone in solution.

Adaptation to an arbitrary number of containers and to a plurality of proteins by simply increasing the number of microvalves and by using a logic for opening these microvalves in which just one microvalve is open at a time, the others being closed. It is therefore thus possible to print an arbitrary number of proteins on a substrate with the invention, without any reduction in contrast compared with the printing of a single protein and without any loss of time, with the proviso of it being possible to have a means of grafting each protein in solution with each protein, this grafting means being suitable for the substrate. The logic may be controlled in particular by a computer, so as to automate as much as possible a printing system according to the invention.

Optional operation without a rinsing line. Indeed, it appears from the description of the first embodiment of the invention that the flow of a solution on the layer contributes to the washing of the first surface when it is active without illumination. This washing applies to the washing of the first fluid by the second fluid when there is a switch from the first to the second configuration of the first embodiment. During the switch, i.e. the change of fluid in contact with the first surface, or switching phase, a fluid mixture is in contact with the first surface; it may then be desirable to turn off the illumination in order to avoid attaching or printing a mixture of proteins. The illumination can be re-established when it is considered that there is, in contact with the first face, only a pure fluid with the accuracy desired for printing, i.e. when a desired chemical contrast for a single protein on the first surface can be achieved. An intermittent illumination can be easily determined by a person skilled in the art on the criterion of the contrast obtained for each protein printed.

The invention is industrially applicable in the field of protein printing on a substrate.

The considerations below also apply to the invention.

It is understood, for the purpose of the present application or here, that said microfluidic system may comprise a circuit for maintaining the substrate under vacuum. This offers the possibility of recovering the treated substrate easily by breaking the vacuum, at the end of printing.

It is understood here that, in accordance with the teaching of the invention, for all its devices, said microfluidic circuit comprises a washing circuit connected to a buffer solution such as a physiological saline or another solution compatible with the proteins to be printed and means for washing said layer with respect to the solutions of the proteins to be printed. In this case, the printing layer may be washed in situ, which makes it possible not to move the substrate with respect to the images of the patterns to be printed, during replacement of a solution of protein to be printed thereon, and makes it possible to maintain great relative printing accuracy between patterns of different proteins or different patterns of the same protein.

It is understood here that, in the uses of devices according to the invention comprising a washing circuit connected to a buffer solution and said washing means, a step consisting in replacing said first aqueous solution with said second aqueous solution so as to bring the second solution and said layer into contact, at said opening, may comprise the following substeps:

replacing said first aqueous solution with said buffer solution, via the washing means, and replacing the buffer solution with the second aqueous solution so as to bring the second solution and said layer into contact, at said opening.

It is understood here that, in a device according to the invention comprising said washing circuit connected to a buffer solution and said washing means, and means for printing a set of N patterns in bijection with a set of N proteins, a practical example of a method for using the device may comprise the following step:

for each protein i, i ranging from 1 to N, to carry out the following substeps:

opening a microvalve i controlling a container i containing an aqueous solution which is photoactivatable, in the sense of an aqueous solution containing at least one photoactivatable molecule, the aqueous solution also containing a protein i, so as to make it possible to bring said layer into contact with the aqueous solution of the protein i, printing the pattern i by illuminating the layer by means of a source, in particular an ultraviolet (UV) source, making it possible to print the protein i on the layer, eliminating the source illumination, closing the microvalve i, and opening a buffer microvalve controlling a buffer container containing a buffer solution for washing the layer of the aqueous solution of the protein i via the washing means.

It is understood here that the invention is also a device for the microstructured grafting of several proteins onto a substrate, which comprises a substrate, a layer, a matrix, a light source, an optical system, a first aqueous solution, a second aqueous solution and a microfluidic circuit, wherein the layer is placed on the substrate, the source illuminates the matrix with the light, the matrix propagates the light in a first structured pattern, the matrix comprises optical means for replacing the first structured pattern with a second structured pattern, the optical system forms, on the layer, a first microstructured image of the first pattern, the circuit contains the first aqueous solution, the circuit comprises an opening for the first solution, the first solution is in contact with the layer at the opening, the circuit comprises microfluidic means for replacing the first solution with the second solution, the layer comprises a polyethylene glycol at its surface, the first solution comprises a benzophenone and a first protein, and the second solution comprises the benzophenone and a second protein, in which device the microfluidic means for replacing the first solution with the second solution comprise means for washing the layer with a buffer solution compatible with the first and second protein, said washing means being capable of washing the layer of the aqueous solution of the first protein.

The invention claimed is:

1. A device for the microstructured grafting of several proteins onto a substrate, comprising:
   a substrate,
   a layer comprising a polyethylene glycol and being placed on the substrate,
   a matrix for propagating the light in a first structured pattern and for replacing the first structured pattern with a second structured pattern,
   a light source for illuminating the matrix,
   an optical system for forming, on the layer, a first two-dimensional microstructured image of the first structured pattern and a second two-dimensional microstructured image of the second structured pattern,
   a first container for receiving a first aqueous solution comprising a first grafting component and a first protein,
   a second container for receiving a second aqueous solution comprising a second grafting component and a second protein, and
   a microfluidic circuit for containing the first aqueous solution, comprising an opening for bringing the first aqueous solution into contact with the layer at the opening,
   wherein the microfluidic circuit is adapted to be filled with the first aqueous solution so as to bring the first aqueous solution and the layer into contact, the first two-dimensional microstructured image of the first structured pattern being formed on the layer by means of the light source in order to photoprint the first protein on the layer,
   wherein the microfluidic circuit is adapted to replace the first aqueous solution with the second aqueous solution so as to bring the second aqueous solution and the layer into contact, the first structured pattern being replaced with the second structured pattern so as to form the second two-dimensional microstructured image of the second structured pattern on the layer by means of the light source in order to photoprint the second protein on the layer, and
   wherein said matrix is a planar two-dimensional matrix of micromirrors, each micromirror being individually controlled and propagating the light by reflection, so that the first and second two-dimensional microstructured images have a number of pixels equal to the number of micromirrors of the matrix.

2. The device as claimed in claim 1, wherein said optical system is a microscope objective.

3. The device as claimed in claim 1, wherein said light source is a laser emitting at an ultraviolet wavelength.

4. The device as claimed in claim 3, wherein said ultraviolet wavelength is 365 nm.

5. A method for the microstructured grafting of proteins onto a substrate using a device as claimed in claim 1 and comprising:
   filling the first container with a first aqueous solution comprising a benzophenone and a first protein,
   filling said microfluidic circuit with said first aqueous solution so as to bring the first solution and said layer into contact, at said opening, and
   forming, by means of said light source, said first two-dimensional microstructured image of said first structured pattern, on the layer, in order to photoprint said first protein on the layer.

6. The method as claimed in claim 5, wherein said first protein is fluorescent.

7. The method as claimed in claim 5, comprising:
   filling the second container with a second aqueous solution comprising the benzophenone and a second protein,
   replacing said first aqueous solution with said second aqueous solution so as to bring the second solution and said layer into contact, at said opening, and
   replacing said first structured pattern with said second structured pattern so as to form the second two-dimensional microstructured image of the second structured pattern on the layer by means of the light source in order to photoprint said second protein on the layer.

8. The method as claimed in claim 5, wherein said second protein is fluorescent.

9. The device as claimed in claim 2, wherein said light source is a laser emitting at an ultraviolet wavelength.

10. A method for the microstructured grafting of proteins onto a substrate using a device as claimed in claim 2 and comprising:
    filling the first container with a first aqueous solution comprising a benzophenone and a first protein,
    filling said microfluidic circuit with said first aqueous solution so as to bring the first solution and said layer into contact, at said opening, and
    forming, by means of said light source, said first two-dimensional microstructured image of said first structured pattern, on the layer, in order to photoprint said first protein on the layer.

11. A method for the microstructured grafting of proteins onto a substrate using a device as claimed in claim 3 and comprising:
    filling the first container with a first aqueous solution comprising a benzophenone and a first protein,
    filling said microfluidic circuit with said first aqueous solution so as to bring the first solution and said layer into contact, at said opening, and
    forming, by means of said light source, said first two-dimensional microstructured image of said first structured pattern, on the layer, in order to photoprint said first protein on the layer.

12. A method for the microstructured grafting of proteins onto a substrate using a device as claimed in claim 4 and comprising:
    filling the first container with a first aqueous solution comprising a benzophenone and a first protein,
    filling said microfluidic circuit with said first aqueous solution so as to bring the first solution and said layer into contact, at said opening, and
    forming, by means of said light source, said first two-dimensional microstructured image of said first structured pattern, on the layer, in order to photoprint said first protein on the layer.

13. The method as claimed in claim 6, comprising:
    filling the second container with a second aqueous solution comprising the benzophenone and a second protein, replacing said first aqueous solution with said second aqueous solution so as to bring the second solution and said layer into contact, at said opening, and replacing said first structured pattern with said second structured pattern so as to form the second two-dimensional microstructured image of the second structured pattern on the layer by means of the light source in order to photoprint said second protein on the layer.

14. The method as claimed in claim 6, wherein said second protein is fluorescent.

15. The method as claimed in claim 7, wherein said second protein is fluorescent.

16. The device as claimed in claim 1, wherein the first grafting component is a benzophenone.

17. The device as claimed in claim 1, wherein the second grafting component is a benzophenone.

* * * * *